Feb. 12, 1957 R. L. BYRUM Plant Pat. 1,566
ROSE PLANT
Filed May 4, 1956
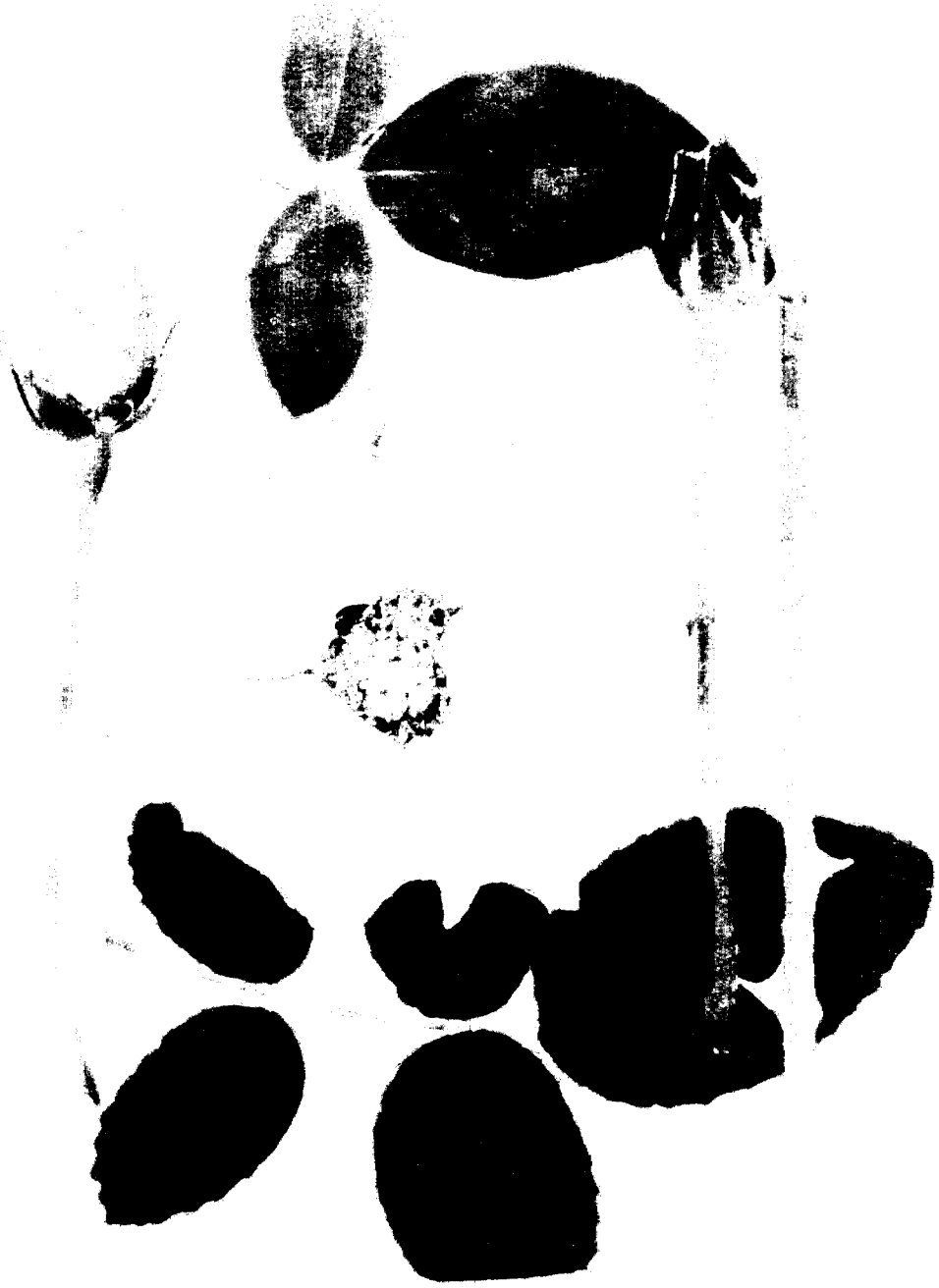
Inventor.
R. L. Byrum
By: Robb & Robb
Attorneys.

United States Patent Office

Plant Pat. 1,566
Patented Feb. 12, 1957

1,566

ROSE PLANT

Roy L. Byrum, Richmond, Ind., assignor to Joseph H. Hill Company, Richmond, Ind., a corporation of Indiana Application May 4, 1956, Serial No. 582,898

1 Claim. (Cl. 47—61)

The present invention relates to a new and distinct variety of rose plant of the hybrid tea class, which was originated by me by crossing the variety "Pink Bountiful" (Plant Patent No. 601) with the variety "Sister Kenny" (Plant Patent No. 1,146).

The primary objective of this breeding was to produce a new rose variety of the hybrid tea type which bears flowers of a color corresponding to those of "Sister Kenny," while at the same time maintaining the good keeping qualities of the latter, combined with a productivity corresponding to that of "Pink Bountiful." This objective was fully achieved, along with other improvements, as evidenced by the following unique combination of features which are outstanding in my new variety:

(1) A very vigorous habit of growth;
(2) Leathery, dark green foliage;
(3) Extra good flower production and keeping qualities;
(4) Short peduncle;
(5) The very uniform color of the flower petals; and
(6) The distinctive red general color tonality of the flowers, varying from signal red in the newly opened flowers to crimson in the 3-day open flowers.

The foregoing characteristics and distinctions definitely differentiate my new variety from its parents, as well as from all other varieties of its class of which I am aware, and asexual reproduction of my new variety by both grafting and budding, as performed at Richmond, Indiana, and in Texas, respectively, shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Koster's Color Guide (hereinafter abbreviated as "Koster"):

Type: Bush; seedling; for greenhouse use.
Class: Hybrid tea.
Breeding: Seedling.
*Seed parent.*—"Pink Bountiful."
*Pollen parent.*—"Sister Kenny."
Propagation: Holds its distinguishing characteristics through succeeding propagations by both grafting and budding.

*Flower*

Locality where grown and observed: Richmond, Indiana.
Flowers borne: One to a stem; on long, strong stems.
Quantity of bloom: Abundant, in greenhouse.
Continuity: Continuous.

Fragrance: Slight. Nature—tea.
Bud:
*Peduncle.*—Short; small; strong; erect. Bark—almost smooth; color—Fern Green, Plate 0862 (Wilson). Thorns—none. Prickles—few; color—Pod Green, Plate 061/3 (Wilson).
Hairs—few; color—Pod Green, Plate 061/3 (Wilson).
*Before calyx breaks.*—Size—medium small. Form—short pointed; with a conspicuous neck; with foliaceous appendages on the surface of the bud and extending beyond the tip of the bud equal to ¼ or more of its length. Color—Scheeles Green, Plate 860/1 (Wilson).
*As calyx breaks (outside of petal).*—Indian Lake, Plate 826/1 (Wilson).
*As first petal opens.*—Size—medium small. Form—short pointed; ovoid. Color: outside—Currant Red, Plate 821/1 (Wilson), with some parts overlaid with Cardinal Red, Plate 822 (Wilson); inside—Blood Red, Plate 820 (Wilson), lightly pencilled with Cardinal Red, Plate 822 (Wilson).
*Opening.*—Opens up well in greenhouse; no unusual characteristics.
Bloom:
*Size (when fully open).*—Medium large; from 3 inches to 3½ inches.
*Petalage.*—Semi-double (2 or 3 rows); from 25 to 30 petals; arranged regularly.
*Form.*—Full and high-centered at first, but becoming open; petals being at first very tightly rolled outward, but becoming loosely rolled outward later at maturity.
Petals:
*Texture.*—Thick; leathery. Inside—satiny; outside—satiny.
*Shape.*—Outside petals—obovate, with apex obtuse. Intermediate petals—obovate, with apex obtuse. Inner petals—obovate, with apex obtuse, and some with 1 notch.

This description of a newly opened flower was made from a rose grown in a greenhouse in the month of October, at Richmond, Indiana:

*Color.*—Outer petal: outside surface—Currant Red, Plate 821/3 (Wilson), slightly overlaid with Cardinal Red, Plate 822/3 (Wilson); inside surface—Cherry, Plate 722 (Wilson), pencilled with Currant Red, Plate 821 (Wilson). Intermediate petal: outside surface—Currant Red, Plate 821/3 (Wilson), slightly overlaid with Cardinal Red, Plate 822/3 (Wilson); inside surface—Cherry, Plate 722 (Wilson), pencilled with Currant Red, Plate 821 (Wilson). Inner petal: outside surface—Currant Red, Plate 821/3 (Wilson), slightly overlaid with Cardinal Red, Plate 822/3 (Wilson); inside surface—Cherry, Plate 722 (Wilson), pencilled with Currant Red, Plate 821 (Wilson).

This description was made from a rose that was open for 3 days in a greenhouse in the month of October, at Richmond, Indiana:

*Color.*—outer petal: outside surface—Crimson, Plate 22/1 (Wilson); inside surface—Crimson, Plate 22 (Wilson). Intermediate petal: outside surface—Crimson, Plate 22/1 (Wilson); inside surface—Crimson, Plate 22 (Wilson). Inner petal: outside surface—Crimson, Plate 22/1 (Wilson); inside surface—Crimson, Plate 22 (Wilson).

*General color effect.*—Newly opened flower—Signal Red, Plate 719/3 (Wilson). 3-days open—Crimson, Plate 22 (Wilson).

*Behavior.*—Persist; normal; no unusual characteristics, but fades to Crimson, Plate 22/2 (Wilson).

*Flower longevity.*—Cut roses grown in greenhouse and kept at living-room temperatures—5 or 6 days in October.

*Reproductive organs*

Stamens: Many; arranged regularly about pistils; tucked in calyx.

Filaments: Medium length; most with anthers. Color—Spinel Pink, Plate 0625/1 (Wilson).

Anthers: Medium small; all open at once. Color—some Tan, Plate #91 (Koster) and some Bistre, Plate #93 (Koster).

Pollen: Abundant. Color—Indian Yellow, Plate #8 (Koster).

Pistils: Many.

Styles: Uneven; medium length; thin; bunched. Color—Rose Red, Plate 724/1 (Wilson).

Stigma: Color—Pure White, Plate #1 (Koster).

Ovularies: Some protruding from calyx.

Hips: Round; with inconspicuous neck; very smooth; with thin walls. Color (before ripening)—Fern Green, Plate 0862 (Wilson).

Sepals: Permanent; moderately short; spear-shaped; curled. Color: inside—Cedar Green, Plate #80 (Koster), overlaid with white fuzz; outside—Scheeles Green, Plate 860/1 (Wilson).

Seeds: Many; medium large.

*Plant*

Foliage:

*Leaves.*—Compound of 3 to 5 leaflets; abundant; medium large; heavy; slightly wrinkled; leathery.

*Leaflets.*—Shape—ovoid. Apex—acute. Base—round. Margin—simply serrate.

*Color.*—Mature: upper surface—near Parsley Green, Plate 00962 (Wilson); under surface—Cedar Green, Plate #80 (Koster). Young: upper surface—Scheeles Green, Plate 860/2 (Wilson), with outer edge of leaf near Oxblood Red, Plate 00823/3 (Wilson); under surface—Scheeles Green, Plate 860/2 (Wilson), very lightly washed with Oxblood Red, Plate 00823/3 (Wilson).

*Rachis (the supporting stem of the compound leaf).*—Medium heavy. Upper side—smooth; grooved. Under side—almost smooth; prickly.

*Stipules.*—Very short; narrow; with short points turning out at an angle of more than 45°.

Growth:

*Habit.*—Bush; upright; much-branched.

*Growth.*—Free; vigorous.

*Canes.*—Medium diameter.

*Main stems.*—Color—some Cedar Green, Plate #80 (Koster), and some Cedar Green, Plate #80 (Koster) overlaid with Tobacco Brown, Plate #88 (Koster). Thorns—many; long; hooked downward; with short, narrow base; color—Tobacco Brown, Plate #88 (Koster). Prickles—several; color—Tobacco Brown, Plate #88 (Koster). Hairs—none.

*Branches.*—Color—Spinach Green, Plate #75 (Koster). Thorns—several; long; hooked downward; with short, narrow base; color—Sap Green, Plate 62/3 (Wilson). Prickles—several; color—Sap Green, Plate 62/3 (Wilson). Hairs—none.

*New shoots.*—Color—Sheeles Green, Plate 860/2 (Wilson). Thorns—several; medium length; hooked downward; with long, narrow base; color—Spinel Red, Plate 0023/2 (Wilson) at base, gradually changing to Pea Green, Plate 61/3 (Wilson). Prickles—several; color—Spinel Red, Plate 0023/2 (Wilson). Hairs—none.

I claim:

A new and distinct variety of rose plant of the hybrid tea class, substantially as herein shown and described, characterized particularly as to novelty by its very vigorous habit of growth, its leathery dark green foliage, its extra good flower production and keeping qualities, its short peduncle, the very uniform color of its flower petals, and the distinctive red general color tonality of its flowers, varying from signal red in the newly opened flowers to crimson in the 3-day open flowers.

No references cited.

Dedication

Plant Pat. No. 1,566.—*Roy L. Byrum*, Richmond, Ind. ROSE PLANT. Patent dated Feb. 12, 1957. Dedication filed Sept. 21, 1971, by the assignee, *Joseph H. Hill Company*.

Hereby dedicates its entire interest in the said patent to the Public of the United States.

[*Official Gazette November 9, 1971.*]